US012566004B2

(12) United States Patent
Wieser

(10) Patent No.: US 12,566,004 B2
(45) Date of Patent: Mar. 3, 2026

(54) ASSEMBLY AND METHOD FOR OPERATING LAMPS WHICH EMIT UV RADIATION WITH INCREASED SAFETY

(71) Applicant: SMART UNITED HOLDING GMBH, Gruenwald (DE)

(72) Inventor: Andreas Wieser, Munich (DE)

(73) Assignee: SMART UNITED HOLDING GMBH, Gruenwald (DE)

( * ) Notice: Subject to any disclaimer, the term of this patent is extended or adjusted under 35 U.S.C. 154(b) by 264 days.

(21) Appl. No.: 18/268,535

(22) PCT Filed: Dec. 22, 2021

(86) PCT No.: PCT/EP2021/087355
§ 371 (c)(1),
(2) Date: Aug. 3, 2023

(87) PCT Pub. No.: WO2022/136578
PCT Pub. Date: Jun. 30, 2022

(65) Prior Publication Data
US 2024/0077221 A1     Mar. 7, 2024

(30) Foreign Application Priority Data

Dec. 22, 2020    (DE) .......................... 102020134679.4

(51) Int. Cl.
*F24F 8/22*        (2021.01)
*A61L 9/20*        (2006.01)
(Continued)

(52) U.S. Cl.
CPC .................. *F24F 8/22* (2021.01); *A61L 9/20* (2013.01); *F24F 11/49* (2018.01); *G01N 21/643* (2013.01);
(Continued)

(58) Field of Classification Search
CPC ....................................................... A61L 9/20
See application file for complete search history.

(56) References Cited

U.S. PATENT DOCUMENTS 9,308,289 B2 * 4/2016 Graff ...................... F24F 7/003
2019/0336629 A1   11/2019 Dobrinsky et al.
(Continued)

FOREIGN PATENT DOCUMENTS

JP        2003112391 A      4/2003
JP        2004182822 A  *  7/2004

OTHER PUBLICATIONS

International Search Report, mailed Apr. 8, 2022 issued in corresponding PCT Application No. PCT/EP2021/087355, Filed Dec. 22, 2021.

*Primary Examiner* — Casey Bryant
(74) *Attorney, Agent, or Firm* — PERRY + CURRIER INC.

(57)                    ABSTRACT

The invention relates to a method and an assembly having a lamp which radiates UV light, radiating the UV light in a main propagation direction, wherein at least one surface which is permanently illuminated by the UV light of the lamp when the lamp is switched on has a region coated with a material which absorbs UV radiation, the shape and dimensions of the coated region being selected such that all the UV radiation impinging on the illuminated surface with an irradiation intensity above a limit value impinges on the coated region.

9 Claims, 2 Drawing Sheets

Figure 1:
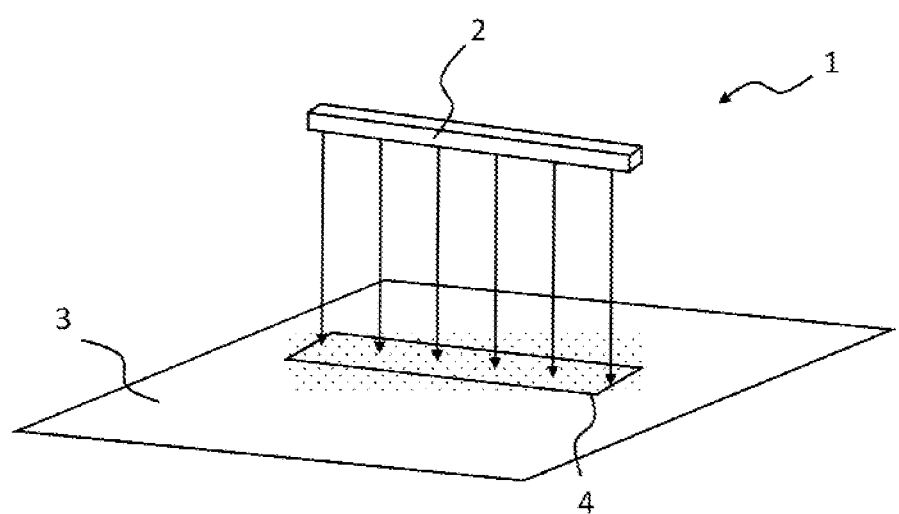

(51) Int. Cl.
    *F24F 11/49*       (2018.01)
    *G01N 21/64*       (2006.01)

(52) U.S. Cl.
    CPC ...... *A61L 2209/111* (2013.01); *A61L 2209/12*
                                                       (2013.01)

(56) References Cited

U.S. PATENT DOCUMENTS

2020/0030478 A1 *   1/2020   Uchimura ................. F24F 8/10
2020/0225088 A1     7/2020   Babaie et al.
2020/0367334 A1   11/2020   Glowczwski

* cited by examiner

ASSEMBLY AND METHOD FOR OPERATING LAMPS WHICH EMIT UV RADIATION WITH INCREASED SAFETY

The invention relates to an arrangement and a method which make it possible to operate lamps emitting UV radiation with increased safety, wherein persons can be present in the rooms decontaminated by the UV radiation at the same time.

Not only since the worldwide Corona pandemic has the health significance of hygiene measures in rooms been known, particularly where a large number of people work together and/or go in and out. Various systems for disinfecting indoor air with UV radiation have already been proposed.

Purpose germicidal radiation is UV radiation. A suitable radiation source is therefore a large lamp that emits UV radiation that is approximately in the wavelength range of 100 to 400 nm. Within UV radiation, the germicidal effect increases from UV-A to UV-B to UV-C with shorter wavelengths. Therefore, a lamp emitting UV-C radiation is particularly suitable, as it specifically emits UV-C radiation that is approximately in the wavelength range of 100 to 280 nm. Preferably, the wavelength range is approximately from 200 to 280 nm, since air is substantially transparent to radiation in this area. Known radiation sources of this type are mercury vapor lamps or light emitting diodes or laser diodes for radiation of corresponding UV light.

However, germicidal UV-C radiation can be harmful to human hanger and skin at excessive doses. Basically, the lamp can be switched off if a person is detected in an area that poses a risk of being directly hit by the UV radiation. A switch is coupled with a corresponding sensor and the radiation source and turns it off when the sensor detects the person.

Suitable sensors for detecting the presence of people are movement detectors such as ultrasonic or radar sensors, which use the Doppler effect when the ultrasonic or radar radiation they emit is reflected off a moving person, or so-called IR-PIR sensors, which detect the changes in thermal radiation in the surrounding of the furniture caused by a moving person. Proximity sensors such as capacitive, optical, ultrasonic or radar sensors that can detect a person in the vicinity regardless of their movement are also suitable. All these approaches follow the same basic idea: if a person is detected near the UV radiation source, the source is switched off. The reaction is thus ultimately dependent on the respective position of the person. The sensors are arranged in such a manner that an approach to the radiation source can be detected. This allows safe shutdown and avoidance of direct irradiation of people by the large lamp.

However, it remains problematic that in order to enable versatile application of such a light for killing germs, safe operation in different scenarios must be made possible. The surroundings of a UV lamp intended for killing germs are very different. For each of these use cases, however, it must be ensured that injury to persons from the operation of the UV lamp is safely avoided. In particular, reflection and scattering of UV radiation from a surface on which the radiation emitted by the UV lamp impinges can also cause harm to persons or animals, even though the sensor system provided for production of operational safety would reliably detect an approach of the person or animal toward the UV lamp.

It is therefore the object of the invention to provide an arrangement as well as a method in which damage to living beings by radiation emitted by the UV lamp can be reliably prevented.

This object is solved by embodiments of the present specification.

The present specification provides various advantageous further embodiments.

The arrangement according to the invention comprises a lamp emitting UV radiation, which emits the UV light in a main propagation direction, wherein at least one surface permanently irradiated by the UV light of the lamp when the lamp is switched on has an area coated with a material absorbing UV radiation. In this case, a shape and dimension of the coated area is selected such or a strip provided with the corresponding material that all UV radiation impinging on the irradiated surface with an irradiance above a limit value hits the coated area.

The radiation emitted by the UV lamp is generated with a strong directional effect, i.e. in a narrow area around the main radiation direction, unless it is to be operated in a room empty of people or living beings in general anyway. This means that the UV lamp only emits radiation in a delimited area, so that people can stay in other areas of the room anyway, as they cannot be hit by the radiation emitted directly by the UV lamp. The coating according to the invention of surfaces, which are irradiated by this bundled or delimited UV light with an intensity above a limit value, with a material which absorbs UV radiation, reliably prevents a hazard to living beings from scattered or reflected radiation. It must be ensured that the material absorbing the radiation is applied to the entire area of the irradiated surface on which UV radiation impinges, in which the irradiance is above a defined limit value.

Limits exist for an uncritical irradiance, for example 0.7 microwatt/square centimeter. This limit value can be selected depending on different specifications or even legal requirements. Based on a known intensity distribution of the light emitted by the UV lamp, it is then possible to determine in which area the surface is to be coated. By adjusting the shape and area of the coated area and applying the appropriate coating in the area thus determined, it is also possible to protect three-dimensionally shaped surfaces lying in the path of the emitted UV light. Thus, by determining the surface actually illuminated with a critical irradiance, the area that could lead to a hazardous reflection or scattering of UV radiation is determined. At least in this area, the UV-absorbing material is then applied. In contrast, areas in which the incident radiation is already below the limit considered critical do not need to be coated.

The invention can be implemented in a particularly simple manner by forming the coated area by means of an adhesive tape provided with the UV light absorbing material. In particular, the adhesive tape can be easily applied to the surfaces to be secured. This allows a flexible solution and the protection can be applied particularly when mounting the UV lamp. But also a strip on which the absorbent material is applied significantly improves the variability in the construction of a system for protection against airborne viruses or other pathogens, without the need to take complicated constructive measures that depend on the particular room.

It is particularly preferred that fluorescent components are further added to the UV light absorbing material, the fluorescence of which is excited by impingement of the UV light. Such fluorescent components bring the advantage that a direct optical control of the emission of UV light by persons can take place, since the operation of the UV lamp can be recognized immediately on the basis of the fluorescent light. This means that people can already see for themselves, without the need for special sensor technology, whether living creatures can move safely anywhere in the room. On the other hand, the fluorescent light can also be used for a power measurement, since the intensity of the incident UV radiation can be determined from a measured intensity of the fluorescent light. Thus, the failure of the system or a part of the system can be determined with the aid of fluorescent components in the coated area.

Optical inspection is particularly easy if the fluorescent components are arranged only in spatially limited partial areas of the coated area. The transitions between the limited partial areas in which fluorescent light occurs and the remaining areas without fluorescent components are preferably sharp. Such edges of objects in an image are easier to detect when using sensors such as cameras.

The additional arrangement of at least one sensor for detecting the fluorescent light is also preferred, since in such an arrangement automated detection of changes from an initial state is possible. In the simplest case, such a sensor can detect an "on" or "off" state of the system by means of the fluorescent light.

The arrangement preferably has an information processing device connected to the at least one sensor. The signal output by the sensor, for example a camera, and dependent on the detected fluorescent light can be compared by the information processing device with a comparison signal, so that if a difference exceeding a limit value is present, the lamp can be switched on in a safe operating state In the simplest case, the safe operating state is to shut down all UV sources. However, more complex evaluations can also be performed. For example, image processing can be performed on a camera image as an output signal from the sensor, allowing spatial resolution of areas where fluorescent light is emitted. The shutdown of the emission of UV light can then be limited to those areas where an unacceptable deviation from the comparison signal is detected. A deviation from the comparison signal always occurs when (at least locally) the situation has changed compared to an initial state that is designated as safe, for example during commissioning. If, for example, despite the UV lamp being switched on, it is detected in certain areas on the basis of a captured image during operation that the fluorescent light decreases in comparison with the reference signal, it can be concluded that there is an object in the beam path of the UV light. In this case, the system can be switched off, at least locally, so that this area is no longer irradiated with UV light.

The comparison signal can be obtained by taking a receptacle after the system is installed and storing the signal recorded by the sensor, or camera, in a memory. This stored signal serves as a comparison signal when further receptacles are taken from the camera (sensor) in later, ongoing operation.

The information processing device can also analyze the difference between the comparison signal and the signal output from the sensor locally/and or with respect to time, and classify an instantaneous operating state of the arrangement based on the analysis result. As indicated above, for example, the sudden local decrease in the intensity of the fluorescent light can be detected as an object in the area of the emitted radiation. On the other hand, a gradual decrease in intensity can also be observed. For this purpose, the measurement results would have to be stored time-resolved. Such a gradual decrease may indicate, for example, that a coating applied a certain time ago is gradually thinning due to wear and tear and thus losing its protective properties.

This is because the decrease in the intensity of the fluorescent light also suggests a decrease in the thickness of the layer containing the absorbing material. Typical application examples would be floors, tables or other objects whose surfaces are mechanically stressed. Cleaning surfaces alone can result in ablation of the coated area.

Depending on the classified instantaneous operating state, a safe operating state corresponding to the classified instantaneous operating state is preferably selected from a plurality of safe operating states. As explained above, for example, a sudden decrease in the measured intensity of the fluorescent light can be recognized as the existence of an object in the beam path, whereas a slow decrease over, for example, a spatially less sharply defined area is more likely to indicate wear. In the first case, if individual segments (for example, groups of illuminants) of the UV lamp or in the case of several lamps arranged in the room, only the relevant part of the lamps can be switched off. If, on the other hand, wear of the absorbent coating is detected, the system can be shut down completely and, if necessary, a maintenance measure can be initiated automatically. The failure of individual illuminants can also be identified as a momentary operating state by such a classification. The individual classes are, for example, tabulated in a memory that is extended to the information processing device and assigned to the signals supplied by the sensor or to their temporal progressions.

Figure 2:
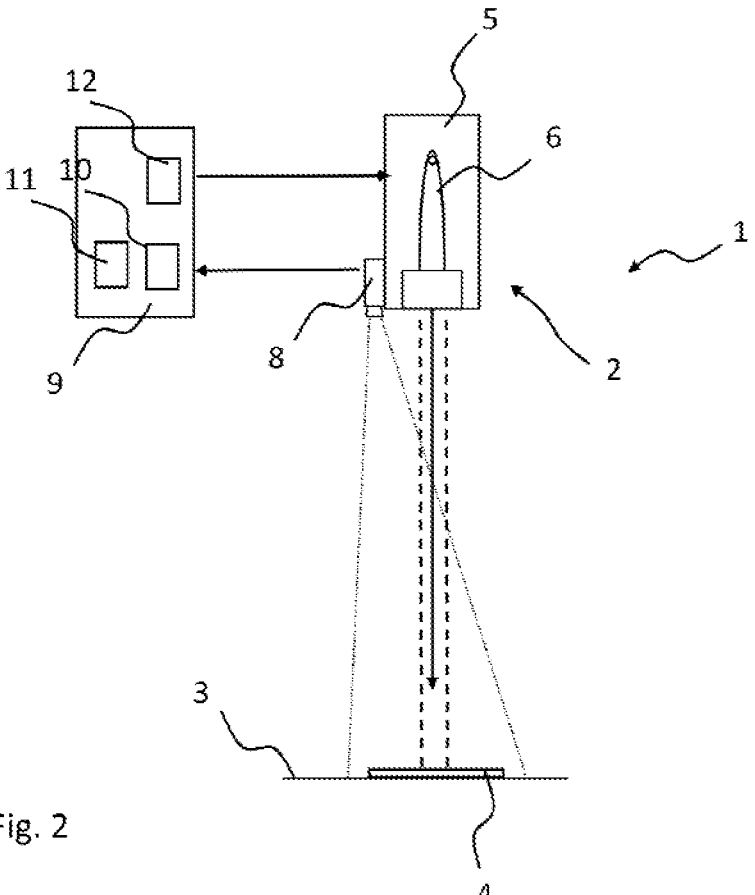
Figure 3:
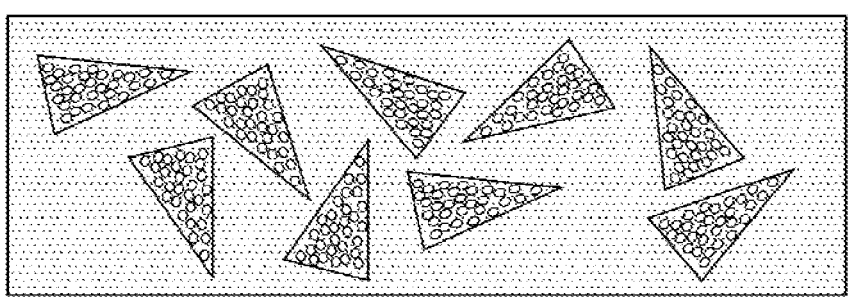
Figure 4:
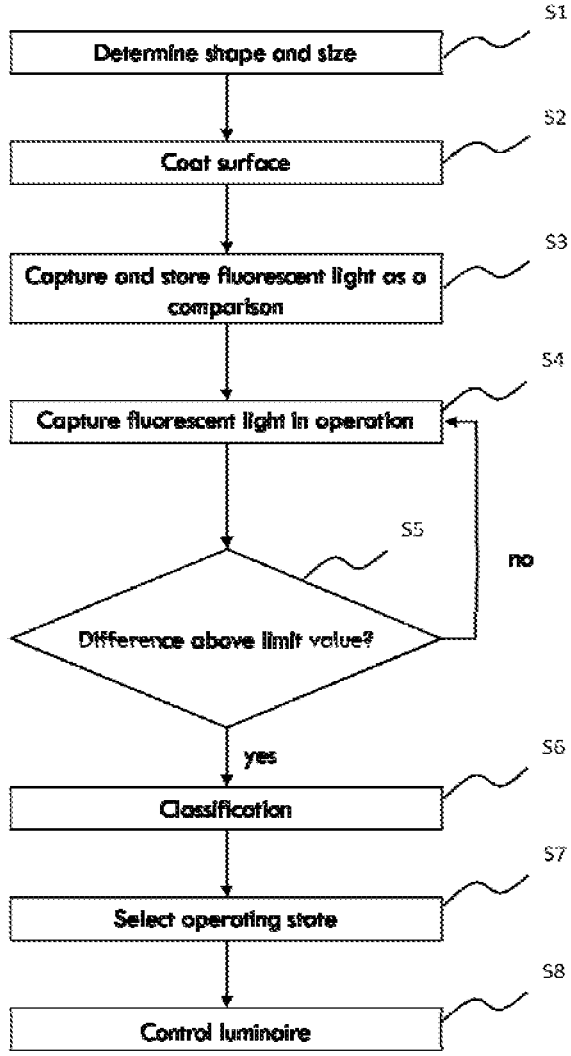

In the following, the invention is explained in more detail with reference to the enclosed drawings by means of a preferred example of an embodiment. In the drawings:

FIG. 1 shows a highly simplified perspective view of the arrangement according to the invention, in which a flat surface is illuminated by UV light from a lamp, FIG. 2 shows a schematic diagram of an arrangement in which the coated area contains fluorescent components whose fluorescent light is detected by a camera for situational awareness, FIG. 3 shows a top view of a coated area with absorbent material and fluorescent components, and FIG. 4 shows a simplified flow chart explaining the method according to the invention.

FIG. 1 shows an arrangement in accordance with the present invention, such as may be used in a room frequented by people. The arrangement 1 comprises a lamp 2 through which UV light, preferably UV-C light, is emitted. The emission of the UV light is schematically represented by the arrows in FIG. 1. The emitted UV light is emitted by the lamp 2 in such a way that it propagates only in the plane characterized by the arrows, wherein the extent perpendicular to the defined plane is narrow compared to the surface of the plane.

Although the preferred application is such a narrow field of radiation that is generated by the lamp 2, the invention is generally applicable whenever UV radiation is emitted in a spatially limited area and this emitted UV radiation impinges on a surface.

In FIG. 1, a surface 3 is shown, which is a flat surface and can be, for example, a floor or a table when the lamp 2 is mounted on a ceiling in a room. Surface 3 generally refers to a surface opposite the lamp in the main direction of radiation, on which the UV light emitted by the lamp 2 impinges. According to the invention, this surface 3 is now provided with a coated area 4, wherein this coated area 4 has UV radiation absorbing material in the layer. The position and extent of the coated area 4 is selected so that all UV radiation emitted by the lamp 2 that impinges on the surface 3 with an irradiance above a specified limit value impinges within the coated area 4.

The arrangement of a coated area 4 with UV radiation absorbing material ensures that even when people are present in a room having the lamp 2, no danger to people can arise from reflected or scattered radiation components of the UV radiation. To enable the lamp 2 to be used to form a barrier to bacteria and viruses in a room, the coated area 4 ensures that even if the nature of the surfaces 3 encountered by the UV light emitted by the lamp 2 is unknown, safe operation is still enabled. The formation of the coated area 4 spatially limited, yet sufficiently extended, allows the use of a UV light emitting lamp 2 in virtually all conceivable room situations. For adaptation, the coated area 4 is adjusted depending on the geometry of the illuminated surface 3 and the irradiance of the incident radiation on the surface 3.

For a more detailed understanding of the mode of operation and in particular the further possibilities of using the coated area 4 also for analyzing the operating state or a failure of individual illuminants a lamp 2 or entire lamps 2, a further schematic diagram is shown in FIG. 2. The arrangement 1, which substantially corresponds to the arrangement 1 already shown with reference to FIG. 1, is shown here in a sectional view, wherein the elements driving the illuminants of the lamp 2 are shown outside the lamp 2. It is understandable that all components required for evaluating or controlling the illuminants of the lamp 2 can also be arranged in the lamp 2 or its housing 5.

In addition to the housing 5, the lamp 2 has a reflector 6 which focuses radiation emitted by one or preferably several illuminants in such a way that the UV radiation generated exits the lamp 2 in the direction of the arrow. The bundling with the aid of optical elements, in the illustrated example the reflector 6, is carried out in such a way that the beam emerges only within the area defined by the two dashed lines on both sides of the arrow indicating the main radiation direction. Together with the illustration of FIG. 1, it can be seen that a narrow "wall" of UV radiation is thus built up as a barrier to pathogens. Passage of viruses or other pathogens from one side of this UV wall to the other side results in the killing of the pathogens. Thus, an effective barrier for viruses or other pathogens is established.

In order to enable the safe operation of such a lamp 2, various safety measures are provided which, for the sake of clarity, are not shown in FIG. 2 and, in particular, can also be used independently of the use of a coated area 4 proposed here. In particular, protective mechanisms are to be provided which are designed on both sides of the radiation field, for example parallel to its boundary planes indicated by the dashed lines. These prevent an object or part of a person's body from entering the UV wall from the side. For this purpose, when intrusion into a security zone is detected, the lamp 2 or a part thereof is switched off so that no more UV radiation is emitted from the lamp 2 in the area where intrusion of an object into the security zone has been detected.

In the simple example shown in FIG. 2, the UV light emitted by the lamp 2 impinges on a surface 3 oriented perpendicular to the main direction of emission. However, the invention is particularly advantageous if this surface 3, or at least parts thereof, does not extend exactly perpendicular to the main radiation direction. With regard to a possible hazard to persons in the room in which the arrangement 1 is present, a perfect specular surface 3 reflecting the UV light in the opposite direction to the main radiation direction would be comparatively uncritical. More dangerous, on the other hand, are situations in which the light incident on the surface 3 is reflected at an angle to the main direction of radiation. In this case, the further safety precautions described above cannot prevent body parts of persons from being hit by the reflected UV light.

In the illustrated embodiment, the coated area 4 contains both UV radiation absorbing material and fluorescent material. The fluorescent material reacts to the incident UV radiation and emits light by spontaneous emission, which is in a different wavelength range that is not critical for living organisms. A camera 8 is arranged on the lamp 2 as a sensor, which generates an image of at least the coated area 4. The image depicts in particular those areas that emit fluorescent light. As will be explained below with reference to FIG. 3, the fluorescent material does not have to be applied to the entire surface of the coated area 4. It is also sufficient if individual partial areas of the coated area 4 have such a fluorescent component.

The image captured by the camera 8 is fed to a controller 9. In addition to a processor 10, which serves as an information processing device, the controller 9 also comprises a memory 11. Comparison information obtained from an image is stored in the memory 11, wherein the image for this purpose is taken in a safe operating state, which exists, for example, when the system is put into operation. In the information processing device, that is, by the processor 10, a comparison between the comparison information and the corresponding information obtained from the currently captured image of the camera 8 can be performed during the normal operation of the UV lamp 2.

From a comparison of the information of these two receptacles, if necessary, also taking into account still further images taken over time, a conclusion can be drawn about the current operating situation in which the UV lamp 2 is being operated. In the simplest case, a decrease in fluorescent light is determined by comparing the information from the current image with the comparison information, and in response, the UV lamp 2 is turned off.

Example of other operating states or deviations from a target irradiance can also be determined based on the captured images from camera 8. For example, a merely local reduction of the intensity of the fluorescent light can also be interpreted to mean that only in a certain area between the actual radiation source, i.e. the lamp 2, and the surface 3 is there an object which locally prevents the irradiation of the surface 3, and thus ultimately the emergence of the fluorescent light. On the other hand, a gradual decrease in illuminance can also be detected, for example, if there is a uniform decrease in the intensity of the fluorescent light. In this case, a maintenance measure could also be triggered if the controller 9 issues a corresponding information signal.

The use of fluorescent components in the coated area 4 also has the advantage that situations in which other safety mechanisms fail still result in safe operation of the arrangement 1. The lamp 2 is set to a safe operating state depending on the evaluation of the image generated by the camera 8. The safe operating state can be that the lamp 2 is switched off as a whole, only partial areas are switched off or, in the case that several lamps 2 are operated together, of a part of the lamps 2.

In the controller 9, a corresponding signal containing the information which parts of a lamp 2 or which lamps 2 are to be switched off is transmitted to the operating device 12. Particularly in the case of multiple lamps 2, there may also be multiple operating devices 12. Alternatively, a multi-channel operating device 12 can be used. On the basis of this signal, the lamp 2 or the multiple lamps 2 are then controlled accordingly by the operating device 12 or the entirety of operating devices 12, so that the area for which a reduction of the fluorescent light was detectable is switched off.

The procedure described above is a considerable safety gain. Although it is possible to use other safety devices to detect the intrusion of objects into the area between the dashed lines and accordingly to switch off the UV light at least locally. However, if only safety zones were applied on both sides of the dashed lines, objects stored in the intermediate space, for example, would not result in a permanent cutoff of UV radiation for that area. An example can be a reflecting object, for example a mirror ball, which is brought into the irradiated area by a person. If this mirror ball is too small to permanently trigger the safety devices on both sides of the irradiated area, the UV light would be switched on again after the hand is pulled out of the safety zone. With the aid of the invention, it is now nevertheless detected that in the image taken by the camera 8 in the area of the mirror ball the fluorescent light is no longer emitted. In response, the arrangement 1 is brought into a safe operating state, i.e. the UV light is switched off at least locally for this area.

To create the coated area 4, an adhesive tape can be used for particularly easy formation of the coated area 4 during mounting of the arrangement 1, on which absorbent material is applied, for example in a printing process, preferably additionally fluorescent material. An example of a pattern that could be used is shown in FIG. 3. FIG. 3 shows only one coated area 4, wherein the coated area 4 has the absorbent material over its entire surface. In addition, portions of the surface, shown in FIG. 3 as triangles of different orientations, have fluorescent material. It can be seen that absorbent material is still present in the area where fluorescent material is applied. This is important because otherwise a reflection could occur in these areas.

The areas in which the fluorescent material is present are only shown as triangles in FIG. 3 as an example. Other geometries are conceivable, as is uniform insertion of fluorescent material. However, the use of sharply defined geometries makes processing in the information processing device easier, as high contrast between fluorescent areas and non-fluorescent areas is easier to see.

FIG. 4 shows a simplified flow chart for performing the method according to the invention. First, in step S1, the shape and size of the area 4 to be coated is determined. This can be done either computationally, if the geometries of the room in which the lamp 2 is to be installed are known, or experimentally, i.e. by measuring the irradiance actually incident on the surface 3. In the next step, S2, the surface 3 is then coated to create the coated area 4, wherein at least UV radiation absorbing material, preferably with portions of fluorescent material is applied for coating.

In addition to the aforementioned coating with the aid of an adhesive tape, or alternatively the application of a varnish containing appropriate pigments, it is also conceivable to mount prefabricated absorber strips or absorber surfaces on carriers.

In the next step, S3, after mounting or applying the coated area 4, an image is taken with the lamp 2 turned on to obtain comparison information. This comparison information is stored in the memory 11 and is available for subsequent evaluation of images captured at a later time.

These further images are captured during regular operation of the lamp 2 in step S4 and transmitted from the camera 8 to the processor 10. By means of the processor 10 as an information processing device, as already described above, an analysis is performed either of the most recently captured image only, or an analysis is performed of the temporal course. It should be noted that in order to avoid errors in the decision, instead of only one image taken last, a plurality of images can also be averaged and from this the information for further analysis can be obtained, which is then evaluated.

To evaluate the image information, step S5 determines whether the deviation from the comparison information exceeds an adjustable limit value. The limit value can be set depending on legal requirements or individual safety requirements. A deviation does not have to be present over the entire surface of the coated area 4; it is sufficient if such a deviation is only detected in a partial area. In particular, spatially resolved detection of deviations is preferable when selective switching off of parts of the illuminants of a lamp 2 is possible.

In accordance with a preferred embodiment, the deviations from the limit value, if applicable including the time course, are used to classify the current operating situation in step S6. Depending on the detected operating situation, the safe operating state to be used is selected in step S7, with which the lamp 2 is then to be operated. For each of the possible classes that can be assigned in step S6, a corresponding safe operating state is stored, for example, in a table in the memory 11.

The information processing device selects the appropriate safe operating state from this table and transmits it to the operating device, or plurality of operating devices 12. The operating device 12 then in turn controls the illuminants of the one lamp 2 or the multiple lamps 2.

As already briefly explained above, it is particularly preferred that additional safety devices are also provided. Regardless of the existence of such further safety devices, however, it must be ensured that the absorbent material has sufficient capabilities to absorb UV radiation from the emitted UV light of the lamp 2 so that the irradiance of the highest radiation intensity emitted by the lamp 2 keeps the possibly still reflected residual light below safety-relevant limit values.

The invention claimed is:

1. A system comprising:

a lamp emitting UV light, which emits the UV light in a light propagation space having a main propagation direction along a plane, wherein the extent of the light propagation space perpendicular to the plane is narrow compared to the surface of the plane of propagation, and wherein said light propagation space is outside the lamp, wherein at least one surface permanently irradiated by the UV light of the lamp when the lamp is switched on has an area coated with a material absorbing UV radiation, wherein a shape and dimension of the coated area are selected such that all UV radiation impinging on the irradiated surface with an irradiance above a limit value impinges on the coated area, wherein the UV light-absorbing material further has fluorescent components, the fluorescence of which is excited by impingement of the UV light, wherein the system further comprises at least one sensor for detecting fluorescent light, and an information processing device which is connected to the at least one sensor and compares a signal output by the sensor and dependent on the detected fluorescent light with a comparison signal and, if a difference exceeding a limit value is present, switches the lamp to a safe operating state.

2. The system according to claim 1, wherein the coated area is formed by an adhesive tape provided with the UV light-absorbing material.

3. The system according to claim 1, wherein the fluorescent components are arranged only in spatially limited partial areas of the coated area.

4. The system according to claim 1, wherein the information processing device is configured to analyze the difference between the comparison signal and the signal output from the sensor and to classify an instantaneous operating state of the system.

5. The system according to claim 4, wherein the information processing device is further adapted to select, depending on the classified instantaneous operating state, from a plurality of safe operating states, an upper safe operating state corresponding to the classified instantaneous operating state.

6. A method for safely operating a lamp emitting UV light, wherein the method comprises the steps of:

emitting light in a light propagation space having a main propagation direction along a plane, wherein the extent of the light propagation space perpendicular to the plane is narrow compared to the surface of the plane of propagation, determining a shape and dimension of an area of a surface irradiated by UV radiation from the lamp emitting UV light such that all of the UV radiation incident on the surface, with irradiance above a limit value, is within the area, and coating the surface at least in a determined area with a UV radiation absorbing material,

wherein fluorescent components are added to the UV light absorbing material, wherein fluorescent light emitted by the fluorescent components is detected when the lamp emitting UV light is switched on, wherein a signal dependent on the detected fluorescent light is supplied to an information processing device, which is compared with a comparison signal by the information processing device, and wherein the lamp emitting UV light is switched to a safe operating state when a difference exceeding a limit value is detected between the comparison signal and the signal output by a sensor.

7. The method according to claim 6, wherein an adhesive tape provided with the UV light absorbing material is applied to form a coated area.

8. The method according to claim 6, wherein the information processing device analyzes the difference between the comparison signal and the signal output from the sensor and classifies a current operating state of the lamp emitting UV light.

9. The method claim 6, wherein the information processing device further selects, depending on a classified current operating state, a safe operating state corresponding to the classified current operating state from a plurality of safe operating states.

* * * * *